United States Patent
Haddad et al.

(10) Patent No.: US 6,233,479 B1
(45) Date of Patent: May 15, 2001

(54) MICROWAVE HEMATOMA DETECTOR

(75) Inventors: Waleed S. Haddad, Dublin; James E. Trebes, Livermore; Dennis L. Matthews, Moss Beach, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/153,642

(22) Filed: Sep. 15, 1998

(51) Int. Cl.$^7$ ................................... A61B 5/05
(52) U.S. Cl. ............... 600/430; 600/534; 600/595; 343/100; 343/718; 343/755; 343/757; 343/761; 343/772
(58) Field of Search ................... 600/430, 595, 600/407, 534; 343/718, 755, 757, 761, 772, 785, 786, 907, 781, 100; 128/653

(56) References Cited

U.S. PATENT DOCUMENTS

| | | | |
|---|---|---|---|
| 3,852,748 | * 12/1974 | Stark | 342/365 |
| 4,168,484 | 9/1979 | Wright, Jr. | 367/59 |
| 4,223,316 | * 9/1980 | Drabowitch | 343/781 P |
| 4,344,440 | * 8/1982 | Aaby et al. | 128/653 |
| 4,407,292 | * 10/1983 | Edrich | 600/430 |
| 4,673,947 | * 6/1987 | Newham | 343/781 CA |
| 5,229,726 | 7/1993 | Kent et al. | 324/632 |
| 5,704,355 | 1/1998 | Bridges | 128/653.1 |
| 5,766,208 | * 6/1998 | McEwan | 600/595 |
| 5,796,363 | * 8/1998 | Mast | 342/22 |
| 5,808,962 | * 9/1998 | Steinberg et al. | 367/7 |

* cited by examiner

*Primary Examiner*—Marvin M. Lateef
*Assistant Examiner*—Jeoyuh Lin
(74) *Attorney, Agent, or Firm*—Alan H. Thompson; Eddie E. Scott

(57) ABSTRACT

The Microwave Hematoma Detector is a non-invasive device designed to detect and localize blood pooling and clots near the outer surface of the body. While being geared towards finding sub-dural and epi-dural hematomas, the device can be used to detect blood pooling anywhere near the surface of the body. Modified versions of the device can also detect pneumothorax, organ hemorrhage, atherosclerotic plaque in the carotid arteries, evaluate perfusion (blood flow) at or near the body surface, body tissue damage at or near the surface (especially for burn assessment) and be used in a number of NDE applications. The device is based on low power pulsed microwave technology combined with a specialized antenna, signal processing/recognition algorithms and a disposable cap worn by the patient which will facilitate accurate mapping of the brain and proper function of the instrument. The invention may be used for rapid, non-invasive detection of sub-dural or epi-dural hematoma in human or animal patients, detection of hemorrhage within approximately 5 cm of the outer surface anywhere on a patient's body.

57 Claims, 2 Drawing Sheets

MICROWAVE HEMATOMA DETECTOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to the detection of blood pooling near the surface of the body, and more specifically, it relates to technology for the diagnosis of sub-dural or epi-dural hematoma.

2. Description of Related Art

At present, there is no non-invasive way to check patients for hematoma other than a paramedic's verbal/tactile evaluation and x-ray computed tomography (CT). A hematoma can exist in a patient with few or no symptoms, and can grow rapidly, killing or rendering the patient comatose within as little as 10 minutes.

In one of the current procedures for screening head injury patients, paramedics or first responders to the scene of an accident evaluate the patient state (through questions and observations of the patient's behavior) and the accident situation (degree of damage to cars, height of fall, etc.). In cases of severe head injury or concussion, there exists a ranking system called the Glasgow coma scale. The patient is ranked based on observation of reflex response, eye movement, breathing, ability to speak, etc. The ranking can be quite inaccurate if the patient is drunk or has other injuries that impact the ranking procedure (i.e. severe loss of blood, patient is in shock, blocked airway, etc.).

In another currently used head injury screening procedure, patients with known head trauma or suspected head trauma are then sent for a CT scan. The decision to order a CT scan is done conservatively, i.e., even if it is not clearly warranted. This is a precautionary measure since a patient with a sub-dural or epi-dural hematoma may not present with clear symptoms at the outset. Sub-dural or epi-dural hematoma can cause the patient to lapse into a coma or go into respiratory arrest. Time is the critical parameter in determining mortality or morbidity that will result from the injury.

The cost of a CT scan is high. A typical head scan is about $500–$800, and can cost much more if the patient must be sedated or closely monitored during the scan. In many cases, many scans of a single patient are necessary to monitor the development of his/her condition.

The total time required for a scan is about 15 minutes using a helical scan device (faster than the standard CT scanners). If the scanner is physically located right in the emergency room, this time can go down to 5 –10 minutes. However, the actual time to diagnose a hematoma (or other problem) is usually limited by patient transportation, preparation and the need to have a radiologist read the scan. If the scan must be sent out of the emergency room for reading, the overall time can be between 30 minutes and 3 hours. A hospital may need to do many CT scans a day. At a typical ER, between 70% and 90% of CT head scans are unnecessary—i.e., are done for precautionary reasons and yield a negative result.

SUMMARY OF THE INVENTION

It is an object of the present invention to provide a Microwave Hematoma Detector for diagnosing blood pooling near the surface of the body and more specifically near the surface of the head.

It is another object of the invention to provide a low cost, non-invasive, portable device for screening head injury patients for the presence and degree of severity of a hematoma.

The Microwave Hematoma Detector can be used immediately at the scene of an injury by a paramedic or first responder, in the emergency room (ER), in local clinics and in hospital intensive care units (ICU) and operating rooms (OR). It allows rapid testing of patients prior to CT scanning, eliminating unnecessary CT scans, or could replace the use of CT for examining head injury victims. It has the potential for saving many lives and reducing long term morbidity for head injury victims by reducing the time of diagnosis. It allows convenient repeated scans to monitor the growth of a hematoma. It has the potential to greatly reduce the medical costs associated with testing and treating head injury victims, as well as reducing the costs of patient rehabilitation and convalescence by reducing the morbidity resulting from current treatment time delays.

The low-cost, Portable Hematoma Detector could completely replace CT for patient screening in the ER. It also has great value for scanning patients that cannot be given a CT scan due to other injuries. This generally means those who must go directly to surgery, i.e., those with life threatening chest or abdominal injuries. The device can be used in trauma centers because it allows immediate care of severely injured or difficult to handle patients such as children.

The invention can be used as a pre-screening device prior to deciding to get a CT scan. A pre-screening device can reduce the number of unnecessary CT's, thereby lowering costs and freeing up the CT scanner for use on the truly critical patient Pre-screening is also very important particularly with children since it is often the case that a child must be anesthetized in order to complete the CT scan Sedation of a patient is undesirable, very expensive, adds risk to the medical care and adds to the time for diagnosis. Reducing the number of unnecessary (negative result) CT scans is therefore of tremendous value and enables much more cost-effective medical care.

Some uses of the invention include (i) detection of sub-dural or epi- dural hematoma, (ii) detection of pneumothorax (air bubble in the thorax) (iii) detection of plaque (occlusion) in the carotid artery, (iv) determination of the perfusion and/or level of necrosis in skin and "skin flap" grafts, (v) detection of anomalies in composite materials for manufacturing quality control and (vi) finding coatings and/or holes on or near the surface of materials for non-destructive evaluation (NDE). The invention may also be used for detection of blood pooling near body surface, detection fluid in sinuses and detection of fluid in lungs. Assessments may be made of burned tissue, infection, tissue damage, "skin flap " i.e. tissue grafts such as discontinuity between grafted part and rest of body and perfusion in tissue in general. The invention is useful in NDE, e.g., thin films, delaminations in fiberglass or composite materials, stealth aircraft materials inspection and inspection of explosives.

DETAILED DESCRIPTION OF THE INVENTION

Figure 1:
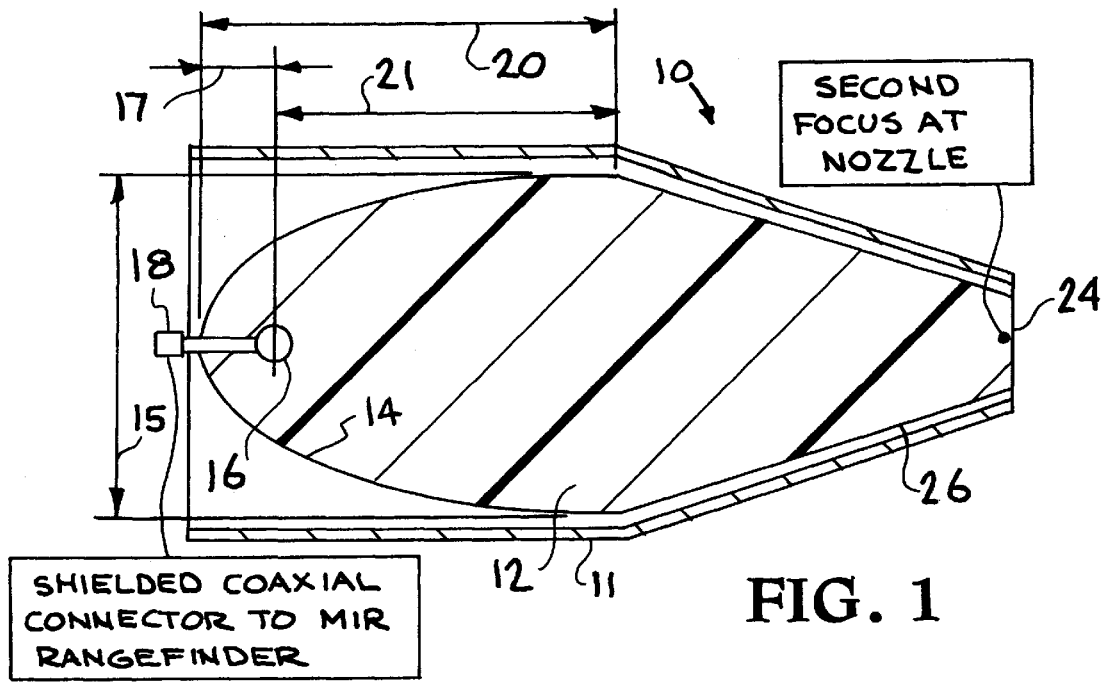
FIG. 1 shows a crossectional view of a cylindrically symmetric near-field antenna of the present invention.

The invention is a near-field microwave probe for medical and other applications. The basic concept includes four generic components. A near-field microwave antenna delivers and confines microwave radiation to a specific region which can be smaller in transverse dimension than the wavelength. Microwave electronics provide swept-range pulse-echo operation. A microprocessor or computer system provides data acquisition, digitization and signal processing, and a user interface. The invention requires one or more specialized algorithms for analyzing the recorded signals.

The near-field microwave antenna may include a variety of configurations such as an air or dielectric filled truncated ellipse, an enclosed GRIN lens with a spherical, parabolic or planar reflector at its back end, and an enclosed linear taper (cone) with a spherical, parabolic or elliptical reflector at its back end.

When using an enclosed linear taper (cone) with a spherical, parabolic or elliptical reflector at its back end, the antenna reflector and taper walls are metal for good reflectivity for microwaves and shielding to keep radiation from propagating into unwanted directions. The structure can be fabricated from sheet metal, such as aluminum, by spin pressing, casting or direct machining, or by creating a form from plastic (by injection molding or other process) then metalizing the inner surface by any standard method. The metal surface should be thicker than about 0.5 mm for good shielding. In any case, the structure should be non-deformable and self supporting so that it is physically robust and maintains it's shape.

The antenna "feed," which is a broad-band microwave feed (there exist a number of standard feeds for broadband microwave transmission/reception), is placed at or near the back focus of the ellipse, or at or near the focus of the reflector for the linear taper.

A variety of dielectric fillings may be used in the antennas, including:

1) Epoxy with the proper dielectric values;
2) Epoxy doped with dielectric particles (higher or lower values);
3) Plastics doped with $TiO_2$ powder or particles of other dielectrics;
4) Silicone doped with $TiO_2$ or other high $n_r$ material;
5) Open cell foam impregnated with gelatin;
6) Open cell foam impregnated with dielectric material with higher $n_r$;
7) Water doped with microballoons or oil emulsion;
8) Gelatin doped with salt or oils to raise or lower $n_r$; and
9) Silicone rubber doped with water globules (high $n_r \sim 9$).

The density of dopant, type of doping material and dopant particle size can be varied in order to tune dielectric properties of the filling material. Materials will be chosen for flexibility or stiffness and/or stability (must not rot or change properties).

The antenna includes a shielded, high frequency, high bandwidth coaxial connector (such as an SMA connector—standard microwave component) at the back of the antenna. A cable or transmission line with a mating connector is used to couple the antenna feed to the electronics.

The antenna housing and/or supporting structure is made of plastic or other light weight rigid material. If the antenna reflectors (like the ellipse and taper, for example) are made of thick enough metal (such as aluminum) so that the structure is self-supporting, then no housing is necessary, but may be desirable for protection.

The invention requires a microprocessor or computer system for data acquisition, digitization, signal processing and to provide a user interface An embodiment of the invention uses a small, on-board digital microprocessor for analyzing the signals from the microwave electronics and triggering a signaling device (e.g., a lamp or a tone) to indicate the presence or absence of a hematoma to the user.

For analyzing the recorded signals, the invention requires one or more specialized algorithms. In one embodiment, a signal processing and recognition algorithm is used to determine whether or not there is a hematoma, and/or to estimate the thickness or severity of the hematoma.

One specific embodiment of a near-field antenna for the hematoma detector is shown in FIG. 1. The figure shows an antenna 10 for use with microwave pulses with a center frequency of ~3.5 GHz. This means the peak wavelength (in vacuum) of the radiation is 8.57 cm. The dielectric filling material 12 with a refractive index of 2 gives an internal wavelength of 4.29 cm. In this specific example, the dielectric filling material is Epoxy which is chosen to have a dielectric constant of ~4 (typical value for epoxy is ~3.6, but varies with type) of which the square root is approximately equal to the refractive index (=2 in this case). The exact value of the filling epoxy's refractive index can be tuned by doping the epoxy before it is allowed to harden with particles of alumina or other materials having higher dielectric constants. Antenna 10 is located within antenna housing 11. The elliptical reflect 14 is designed so that the diameter 15 is 10 cm at its minor axis and the vertex 17 of the ellipse is ¼ wavelength=1.07 cm away from the first focus and the RF feed 16 is located at the focus to optimize the efficiency of the design. A shielded coaxial connector 18 provides a connection between a MIR rangefinder (not shown) and RF feed 16. The major axis 20 of elliptical reflector 14 is 122 mm. The distance 21 from the RF feed 16 along the long axis to the center of the ellipse is 111.3 mm. Elliptical reflector 14 has a second focus at the nozzle 24 of linear tapered cone 26. The distance along the long axis from the center of the ellipse 14 to the second focus is 111.3 mm. Antenna nozzle 24 has a diameter of 25 mm. Linear tapered cone 26 is made of a metallic reflector. The specific dimensions listed are provided as one example of a specific antenna design.

There are at least four (4) alternate antenna designs which can be used for the hematoma detector. All of these designs provide sub-wavelength localization of the radiation emitted by the hematoma detector and therefore allow comparable localization of the hematoma within the head. The 4 designs are (i) an air filled truncated ellipse, (ii) a dielectric filled truncated ellipse, (iii) an enclosed microwave GRIN lens and (iv) an enclosed dielectric filled linear taper with a simple reflector (condenser).

The truncated ellipse designs represent the most efficient collectors and transmitters of microwave radiation to and from the sub wavelength aperture. The GRIN lens design allows a compact efficient antenna to be built and the linear taper design is inefficient, but functional and the simplest to manufacture. Efficiency is desirable for the antenna, but not absolutely necessary since micropower-impulse radar (MIR) devices provide sufficient power and regardless of the antenna design, the transmitter will be adjusted so that very low power is coupled into the patient's head. The approximate average power level required to be actually radiated at the antenna tip (impinging on patient's head) is on the order of 1 to 20 milliwatts [Note: a portable cell phone transmits 600 milliwatts].

An embodiment of the invention includes a low power, battery operated, pulsed microwave transmitter/receiver capable of pulse-echo ranging, i.e., a pulsed transmitter with a gated receiver circuit capable of swept range gating. In general, the hematoma detector can work with other (than MIR) types of microwave sources including pulsed, swept continuous wave (cw), cw only and modulated cw. Examples of the microwave electronics usable in the present invention are described in U.S. Pat. No. 5,757,320 titled "Short Range, Ultra-Wideband Radar with High Resolution Swept Range Gate" which is incorporated herein by reference.

In one embodiment, the source of RF pulses is a single board MIR range finder, or any other microwave circuitry capable of producing short (60 to 200 ps wide in time) pulses and able to perform swept-range acquisition of the reflected (returned) pulses, and which is designed to be used with a single antenna for both transmission and reception of RF pulses. The single board range finder provides all the necessary electronics to generate and transmit pulses, and contains a time swept receiver circuit which analyzes the returned pulses in the time domain. The output is an analog voltage signal which represents the return pulses as a function of time between transmission and reception (or range). Typically the system is preprogrammed to sweep over a certain range (or time delay), and the sweep can be executed at 40 Hz. The sweep can also be triggered via an external input from a computer or other electronic device. The trigger is a simple high or low voltage applied to an input terminal on the MIR board.

For the hematoma detector, the range sweep is set in the range of 20 to 50 cm in air which corresponds to about 2.5 to 7.5 cm in the body. In terms of time delay between transmit and receive, this range corresponds to 67 ps to 167 ps. At all points in range (time delay), multiple pulses can be averaged if necessary in order to increase signal-to-noise (this is a feature of the typical MIR rangefinder circuitry).

Figure 2:
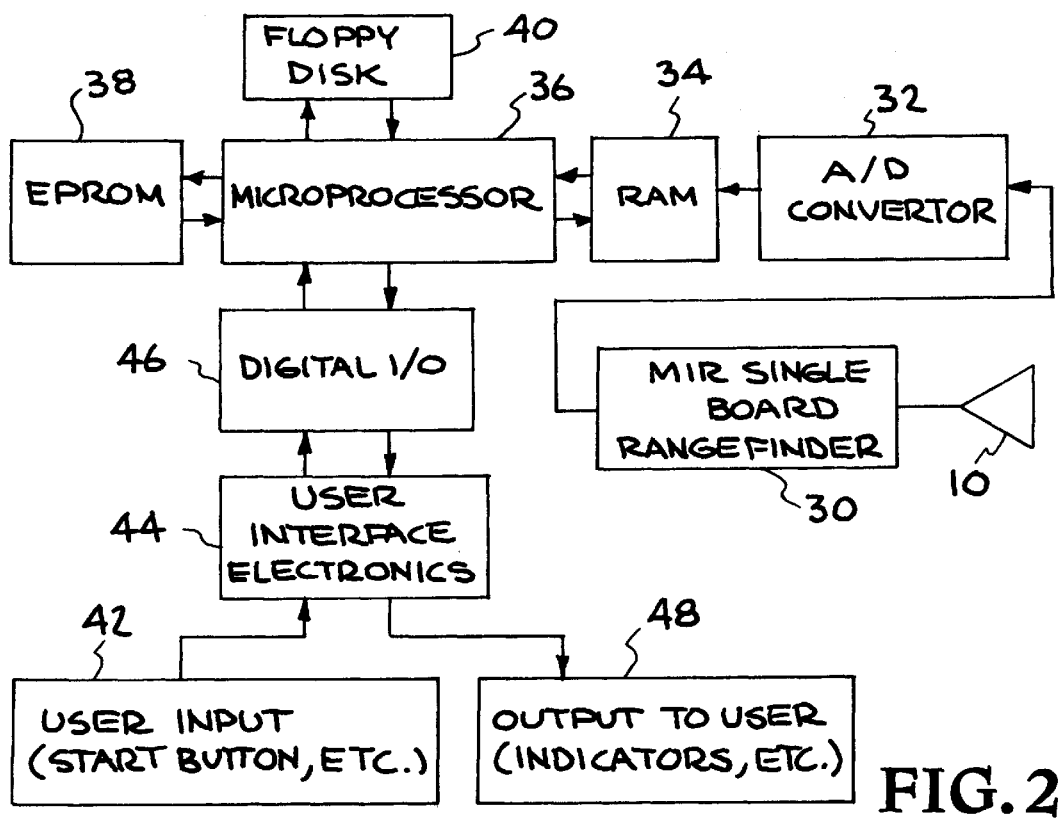
FIG. 2 is a block diagram of the electronic components of the signal acquisition, processing and user interface circuitry.

Referring to FIG. 2, the analog output of the MIR board 30 is digitized by means of an A/D converter circuit 32 (this is a standard component) and stored in RAM 34 to be accessed and processed by the on board microprocessor 36.

The microprocessor 36 can be one of many which are commercially available, however one simple to implement design would be a pre packaged Intel Pentium computer system (a complete PC in a box) similar to the so-called belt-worn computers. This machine has a PCMCIA card slot which can be used to drive a National Instrument DAQ 700 card. This card provides digitization of the signals from the MIR board as well as offering lines which can be used to trigger the range sweep and data acquisition.

The small full-blown PC can be easily programmed using standard software tools. Signal recognition algorithms can be developed on standard PC platforms then downloaded to the standard compact PC which is part of the hematoma detector. The on-board PC has its own battery pack which is independent of that used to power the MIR board.

The EPROM 38 shown in FIG. 2 is used to store both the program which implements the signal processing algorithm and handles the user interface as well as characteristic hematoma signals which are used by the algorithm in analyzing the signals received from the MIR electronics (see algorithm section below). The floppy disk 40 is present as a means for storing patient data and possibly the raw scan data from the hematoma detector for further analysis and/or comparison with other scans at a later time. It is also used as a convenient means by which to upgrade the on-board software if necessary. The EPROM is not necessarily appropriate if the PC in a box is used as the processor. The user input 42 (e.g., a start button, etc.) is connected to user interface electronics 44. A digital input/output device 46 transmits signals from the user interface electronics 44 to the microprocessor 36, and transmits signals from the microprocessor 36 to the user interface electronics 44, which then transmits signals to the output indicator 48.

The hand-held version of the hematoma detector has a special handle on the outside of the casing making it easy for the user to hold while scanning over the patient's head. A temporary push button switch is built into the handle. The user must press this button to turn on transmission of microwaves and trigger a range sweep, thus recording a signal for a particular location on the patient's head. The system is off when the button is not depressed. This is both a safety and power saving feature. Once the button is pressed, the user is signaled by means of two different lamps or tones that the scan has begun, and later, that the scan and processing of the signals has finished (the tone signaling the start of the scan is optional). Immediately thereafter, the user is signaled as to whether or not a hematoma was detected.

In it's simplest form, detection of a hematoma is indicated by either a red versus green lamp or a tone which is emitted every time the user presses the button to take a signal. More sophisticated versions of the device may have a meter (either string of LED or galvanometer/needle type) which indicates the thickness of the hematoma based on the analysis of the received signal. An optional feature is the on-board floppy disk drive. Both the raw scan data as well as the processed signal results (yes/no hematoma or hematoma thickness) as a function of position in the head scan can be stored automatically on the floppy disk for future processing, comparison or archiving. There can also be an input device such as a keyboard that connects to the hematoma detector so that the user can enter patient information such as name, date, location, etc. to be stored on the floppy disk with the scan data.

A number of sensor output options are available. The use of different LEDs (e.g., a red and a green light) could indicate the present or absence of a hematoma. A meter could show signal strength or be used as a hematoma thickness gauge. Analog or digital output could provide storage mapping. The sensor output could provide built in memory of mapping which is downloadable. As part of the detection algorithm, an on board comparison can be made of signal at different points. A sensor could be located in the nozzle tip (e.g., a capacitive sensor) to ensure proper contact and angle with respect to the head. Mechanical stabilizer or constraints could also be provided to ensure proper contact and angle to the head. Capability (in memory) can be provided for storing and labeling data from multiple patients and for automatic data file numbering/labeling. An automatic position reader (i.e., bar codes) could also be provided at each reading point.

The MIR board battery as well as the battery for the PC or microprocessor are rechargeable NiMH batteries. A special charging circuit can be built to handle charging both batteries so that there is a single plug for charging the hematoma detector. The two power supplies could also be consolidated so as to run off of a single battery pack.

The computer system, battery pack details, and A/D converter are all standard, readily available technology.

One embodiment of the hematoma detector includes a special device which allows calibration of the device on location by the user. This device is a standard object which when put against the antenna nozzle and tested by triggering the hematoma detector (as is done at a single scan point on a patient's head) produces a known signal. This known signal is stored in the hematoma detector's memory (EPROM). The user can execute a calibration by placing the standard calibration object against the nozzle and pressing a special button or otherwise switching the device into calibration mode to perform the calibration check. The recorded signal is compared (using an algorithm similar to that for hematoma detection) with the known calibration signal and the user will be notified if the calibration is acceptable or not. It may even be possible to design a system that uses the calibration signal to adjust itself automatically for optimum accuracy. The calibration device consists, in its simplest embodiment, of several layers of materials of varying dielectric constants. The calibration device could be mounted into the storage case for the detector or could be a separate hand held device. It could be an active device including output measurement/recording The following algorithm may be used with the hematoma detector. It is not the only possible method for processing the signals generated by the device and determining the existence/severity of the hematoma. The algorithm presented uses data obtained from laboratory experiments in the form of a set of characteristic hematoma signals from hematomas of different thicknesses and a predetermined threshold value which can be used for judging whether or not a hematoma signal from an actual patient represents a real blood pool or not.

1. The micro-impulse radar (MIR) (or other pulsed, swept range microwave) device is triggered.

2. Several full range sweeps are performed and the return signals are acquired. Example: execute 10 range sweeps and record the returned signals, $S_1$ through $S_{10}$. At a 40 Hz sweep rate, this takes 0.25 seconds.

3. Average the returned signals.

$$S_a = \frac{1}{N}\sum_{i=1}^{N} S_i$$

4. Subtract the background signal $S_b$ from $S_a$ and store the resulting processed signal $S_p$ in memory (EPROM): $S_p = S_a - S_b$. Background may be recorded in open space or with a calibration device as discussed herein.

5. Compare the processed signal $S_p$ with stored characteristic hematoma signals $C_i$ which reside in the microprocessor memory (EPROM). The characteristic signals represent "standard" signals from hematomas of different thicknesses, and are based on the results of laboratory tests. These signals are kept and used in order of increasing thickness and weighted so as to normalize them in terms of their relative amplitudes, i.e.

$$\sum_{t=0}^{M} C_i(t) = 1$$

where M is the number of time points in the digitized signal waveform (Note: summing over M is the digital version of integrating over t).

If, for example, we consider 5 characteristic hematoma signals $C_1 \ldots C_5$, the comparison algorithm will produce 5 scalar values, one for each characteristic signal $I_1 \ldots I_5$, where:

$$I_i = \sum_{t=0}^{M} S_p(t)C_i(t)$$

6. Estimate the hematoma thickness by determining which value of I is the largest=$I_{max}$. This can be done simply by finding the maximum value of I, or a more accurate estimate of the hematoma thickness can be made by interpolating between I values using a standard spline or other fitting routine.

7. Obtain the maximum value of $I=I_{max}$ and apply a threshold at value T to determine whether or not the hematoma is "real."

For example, if $I_{max}$ is greater than or equal to T then trigger the hematoma indicator. If $I_{max}$ is less than T then trigger an indicator showing there is no hematoma. Alternatively, the user can be given an indication of the actual thickness of the hematoma by displaying the thickness value associated with the value $I_i=I_{max}$, and/or an indication of the certainty of the presence of a hematoma by displaying a scaled value based on the actual value of $I_{max}$.

Figure 3:
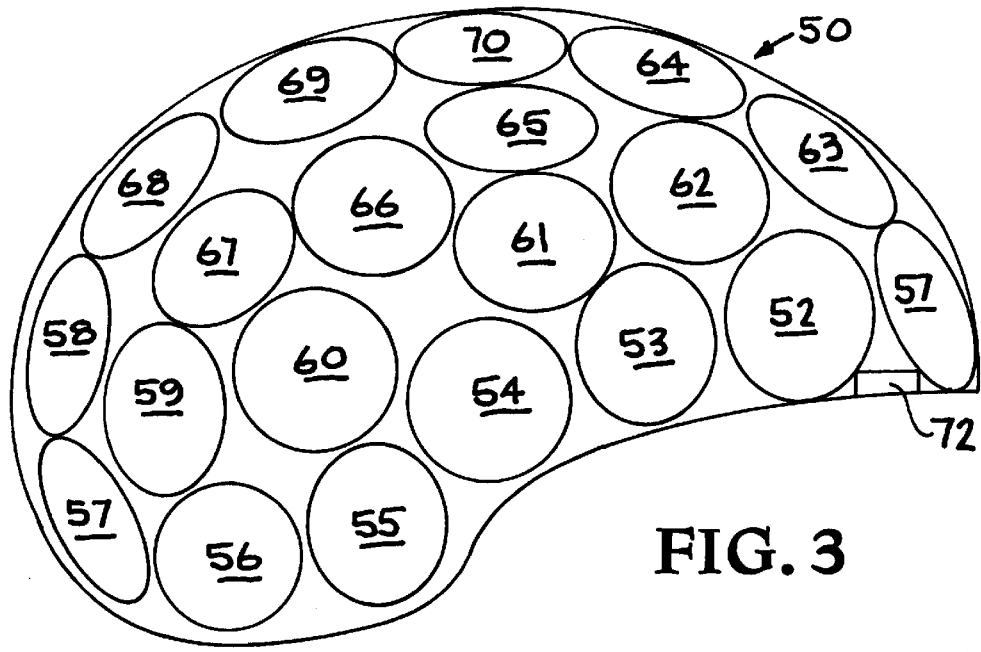
FIG. 3 shows a sketch of the dielectric cap with scan map for use with the microwave hematoma detector.

Referring to FIG. 3, the hematoma detector cap 50 has marked scan points which can be numbered to direct the user in performing the scan of the entire patient's head. The scan points 51–70 can be separated by a distance equal to the diameter of the antenna aperture to ensure complete coverage of the head when scanned. The antenna may be inserted into a mechanical device for automatically scanning a structure such as the head.

The cap is made of a firm, but compliant and stretchable material which also has a dielectric function with a real part of the refractive index close to that of the antenna filling material (~2 for the specific antenna example shown in FIG. 1). The shape of the cap is chosen so that it covers the entire region of the head which must be scanned to ensure that all critical areas of the head are tested. Caps come in a range of sizes to accommodate patient head size variation. The user selects a cap which fits the patient snugly, but not so tightly as to cause discomfort. The cap is stretched over the patient's head, compressing the hair and providing a clean smooth surface over which to do the scan.

An identification device 72, such as a bar code, semiconductor identification chip or microwave discernible identification pattern may be incorporated into the cap. In one embodiment, microwaves produced by the near-field microwave antenna are reflected by the identification device and read by the microprocessor, computer system or other means electrically connected to the antenna, for data acquisition, digitization, signal processing and for providing a user interface. The hematoma detector may be configured to operate only if an authorized cap is used. This will insure correct impedance matching between the antenna and the cap, and prevent incorrect readings which could result from the use of an unauthorized cap.

FIG. 3 shows a sketch of the dielectric cap with scan map for use with the microwave hematoma detector. Before starting a scan of a patient, the cap must be placed over the patient's head. To perform a head scan, the detector nozzle is placed at each marked scan point on the cap in sequence and a reading is taken at each point. The result at each scan point can be displayed immediately, and/or stored into memory for further processing. In addition, the stored data can be displayed as a low-resolution 2-D surface map.

Figure 4A:
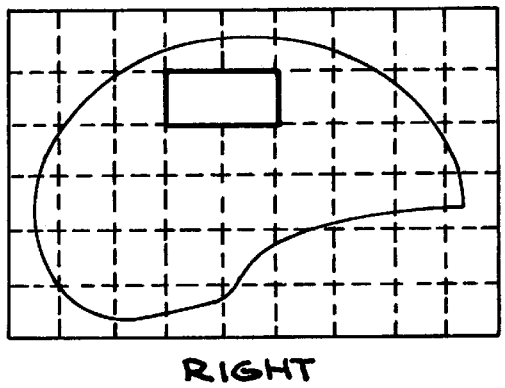
FIGS. 4A–C show the 2-D surface mapping display possible with the microwave hematoma detector.
Figure 4B:
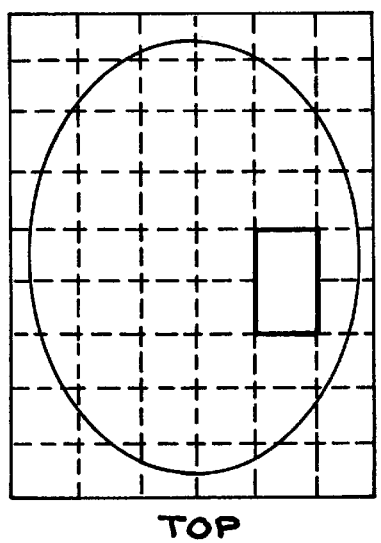
Figure 4C:
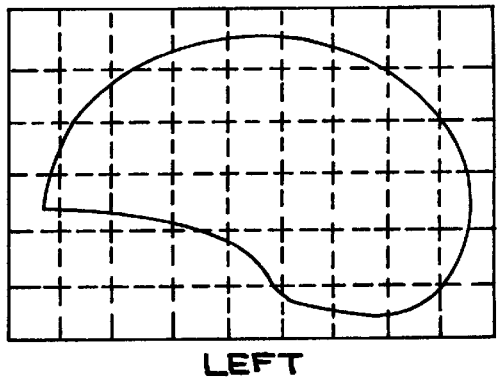

FIGS. 4A–C show the 2-D surface mapping display possible with the microwave hematoma detector. Because the user follows a scan map which is marked on the dielectric cap (placed over the patients head before scanning), it is possible to have the on-board computer store the results obtained at each scan point on the head. Once the full scan of the entire head is completed, the stored information can be converted to a graphical map as shown above which indicates approximate location and size of the hematoma, as well as an estimate of the severity/depth of the blood pool (indicated by the color of the highlighted boxes on the map). The map shown above can be displayed on a portable LCD screen which is built onto the hematoma detector itself, or can be produced on a separate display or computer system after the stored data in the memory of the hematoma detector is downloaded. FIGS. 4A–C shows the right, top and left views respectively of a 2-D surface mapping display.

Properties of the skull cap include:

provides dielectric matching;

flattens hair;

protects sensors from blood etc.;

protects patient's head;

reduces friction between head and device;

provides a "road map" for the scan;

has marked stop or check points at which to take the readings;

specifies a pre-determined scan sequence;

is disposable;

is elastic one size fits most, different sizes possible; and may provide different "road maps" for different applications if necessary or helpful In operating the hematoma detector, the scan is performed by first placing the detector nozzle firmly against the surface of the cap at scan point 51 as shown in FIG. 3. Proper placement of the nozzle is indicated by uniform contact with the cap all around the nozzle. The user then presses the "on" button, triggering the device to record the signal at that location. The user holds the device in place and waits briefly for the detector to indicate that signal acquisition and processing is complete. This is indicated by either a lamp or a tone again as to whether a hematoma was detected at this location. The user then repositions the device at the next scan point and repeats the process. Several readings can be taken at each point to increase confidence in the determination made. The total time spent at each scan point for a single reading will be (estimated) less than or equal to 1 second. This will allow a complete head scan to be carried out in approximately 1 to 5 minutes, depending on the resolution (size of the detector nozzle) of the device.

Pneumothorax is essentially an air pocket that forms in the chest between the lungs and the chest wall. Another embodiment of the invention is used to detect the presence of a pneumothorax. The most common cause of the pneumothorax is a puncture or tear in the lung which causes air to leak through into the chest cavity. The condition can be deadly and is often difficult to detect, especially in the field. This is a particular problem in military medicine. Injuries sustained during battle often result in soldiers (victims) with pneumothorax.

The conditions under which medics must work make it extremely difficult to detect the presence of pneumothorax. This is a problem on and off the battlefield as well as in medivac situations. Many soldiers die in the field or during transport due to undetected pneumothorax. On the other hand, if the condition is detected, medics are prepared to administer a simple, life saving treatment by inserting a chest tube. The insertion of a chest tube is relatively easy, but it involves opening a hole directly in the chest—a very invasive procedure. If the insertion of the chest tube is not warranted, it is highly undesirable, and possibly deadly to the patient. This is especially true in cases in which the victim has other injuries—a very common situation on the battlefield. It is therefore of great important to have a quick, reliable, portable means of determining if a victim has a pneumothorax.

Currently, battlefield medics use oversimplified and unreliable methods of determining if an injured soldier has a pneumothorax. These are basically looking at and listening to the victims chest and checking for asymmetry.

The portable microwave pneumothorax detector (PMPD) is a hand-held device designed to non-invasively and rapidly detect the presence of (or confirm the absence of) pneumothorax (an air pocket in the chest cavity) in a human patient. This is of critical importance to the military as a tool for the battlefield medic, but can find use in civilian medicine as well. This device is based on the same technologies used for the non-invasive microwave hematoma detector. In addition to the detection of pneumothorax, the invention can be used for the detection of a collapsed lung and for the detection of air pockets in the body anywhere dose to the surface (within ~6 cm).

Changes and modifications in the specifically described embodiments can be carried out without departing from the scope of the invention, which is intended to be limited by the scope of the appended claims.

What is claimed is:

1. A near-field microwave probe, comprising:

a near-field microwave antenna to deliver and confine microwave radiation to a specific region;

microwave electronics electrically connected to said antenna, wherein said microwave electronics provide swept-range pulse-echo operation;

first means, electrically connected to said antenna, for data acquisition, digitization, signal processing and for providing a user interface, wherein said first means produces recorded signals;

second means for analyzing said recorded signals; and a housing for containing said near-field microwave antenna, said microwave electronics, said first means and said second means.

2. The near-field microwave probe of claim 1, wherein said microwave electronics produce microwave radiation having a wavelength, wherein said specific region is smaller than said wavelength.

3. The near-field microwave probe of claim 1, wherein said near-field microwave antenna comprises a configuration selected from a group consisting of an air or dielectric filled truncated ellipse, an enclosed GRIN lens with a spherical, parabolic or planar reflector at its back end and an enclosed linear taper (cone) with a spherical, parabolic or elliptical reflector at its back end.

4. The near-field microwave probe of claim 1, wherein said near-field microwave antenna comprises an air filled truncated ellipse.

5. The near-field microwave probe of claim 1, wherein said near-field microwave antenna comprises a dielectric filled truncated ellipse.

6. The near-field microwave probe of claim 5, wherein said ellipse comprises a back focal point, wherein said near-field microwave antenna comprises a broad-band microwave feed placed at or near said back focal point.

7. The near-field microwave probe of claim 1, wherein said near-field microwave antenna comprises an enclosed GRIN lens with a spherical reflector at its back end.

8. The near-field microwave probe of claim 1, wherein said near-field microwave antenna comprises an enclosed GRIN lens with a parabolic reflector at its back end.

9. The near-field microwave probe of claim 1, wherein said near-field microwave antenna comprises an enclosed linear taper (cone) with a spherical reflector at its back end.

10. The near-field microwave probe of claim 1, wherein said near-field microwave antenna comprises an enclosed linear taper (cone) with a parabolic reflector at its back end.

11. The near-field microwave probe of claim 1, wherein said near-field microwave antenna comprises an enclosed linear taper (cone) with a reflector at its back end, wherein said reflector is selected from a group consisting of a spherical reflector, a parabolic reflector, and an elliptical reflector, wherein said reflector and the walls of said enclosed linear taper comprise metal for good reflectivity for microwaves and shielding to keep radiation from propagating into unwanted directions.

12. The near-field microwave probe of claim 11, wherein said metal is at least 0.5 mm thick for good shielding.

13. The near-field microwave probe of claim 10, wherein said reflector comprises a focal point, wherein said near-field microwave antenna comprises a broad-band microwave feed placed at or near said focal point.

14. The near-field microwave probe of claim 1, wherein said near-field microwave antenna comprises a dielectric filling.

15. The near-field microwave probe of claim 1, wherein said near-field microwave antenna comprises an epoxy.

16. The near-field microwave probe of claim 1, wherein said near-field microwave antenna comprises an epoxy doped with dielectric particles.

17. The near-field microwave probe of claim 1, wherein said near-field microwave antenna comprises a plastic doped with $TiO_2$ powder.

18. The near-field microwave probe of claim 1, wherein said near-field microwave antenna comprises a plastic doped with particles of other dielectrics.

19. The near-field microwave probe of claim 1, wherein said near-field microwave antenna comprises silicone doped with high $n_r$ material.

20. The near-field microwave probe of claim 1, wherein said near-field microwave antenna comprises silicone doped with $TiO_2$.

21. The near-field microwave probe of claim 1, wherein said near-field microwave antenna comprises an open cell foam impregnated with gelatin.

22. The near-field microwave probe of claim 1, wherein said near-field microwave antenna comprises an open cell foam impregnated with dielectric material with higher $n_r$.

23. The near-field microwave probe of claim 1, wherein said near-field microwave antenna comprises a water doped with microbubbles or an oil emulsion.

24. The near-field microwave probe of claim 1, wherein said near-field microwave antenna comprises a gelatin doped with oils to raise or lower $n_r$.

25. The near-field microwave probe of claim 1, wherein said near-field microwave antenna comprises a gelatin doped with salt and oils to raise or lower $n_r$.

26. The near-field microwave probe of claim 1, wherein said near-field microwave antenna comprises a silicone rubber doped with water globules.

27. The near-field microwave probe of claim 1, wherein said near-field microwave antenna comprises a dielectric filling material, wherein said dielectric filling material comprises a dopant having a density and a particle size, wherein said dopant, said density and said particle size are variable in order to tune dielectric properties of the filling material.

28. The near-field microwave probe of claim 1, wherein said first means, comprises a microprocessor.

29. The near-field microwave probe of claim 28 further comprising a signaling device for indicating the presence or absence of a hematoma to a user, wherein said microprocessor comprises an on-board digital microprocessor for analyzing said recorded signals from said microwave electronics and triggering said signaling device to indicate the presence or absence of a hematoma to the user.

30. The near-field microwave probe of claim 29, wherein said signaling device is selected from a group consisting of a lamp, an audible tone a depth indicator, a severity indicator and a 2-D surface map.

31. The near-field microwave probe of claim 1, wherein said microwave electronics are selected from a group consisting of a pulsed microwave transmitter/receiver capable of pulse-echo ranging and a pulsed microwave transmitter with a gated receiver circuit capable of swept range gating.

32. The near-field microwave probe of claim 31, wherein said microwave electronics include a battery operated microwave transmitter.

33. The near-field microwave probe of claim 31, wherein said microwave electronics include a battery operated microwave transmitter/receiver.

34. The near-field microwave probe of claim 1, wherein said microwave electronics comprise a pulsed microwave transmitter/receiver capable of pulse-echo ranging.

35. The near-field microwave probe of claim 1, wherein said microwave electronics comprise a pulsed microwave transmitter with a gated receiver circuit capable of swept range gating.

36. The near-field microwave probe of claim 1, wherein said microwave electronics comprise a source of RF pulses.

37. The near-field microwave probe of claim 1, wherein said microwave electronics comprise a single board micro-impulse radar (MIR) range finder.

38. The near-field microwave probe of claim 1, wherein said microwave electronics comprise microwave circuitry capable of producing pulses having a time duration within a range of 60 ps to 200 ps.

39. The near-field microwave probe of claim 38, wherein said microwave electronics comprise means for performing swept-range acquisition of reflected (returned) pulses, and further comprise a single antenna for both transmission and reception of RF pulses.

40. The near-field microwave probe of claim 38, wherein said microwave electronics comprise means for performing swept-range acquisition of reflected (returned) pulses, wherein said swept-range acquisition is within the range of 20 to 50 cm in air which corresponds to about 2.5 to 7.5 cm in the body, wherein said microwave electronics further comprise a single antenna for both transmission and reception of RF pulses.

41. The near-field microwave probe of claim 1, wherein said microwave electronics comprise means for outputting an analog voltage signal which represents the return pulses as a function of time between transmission and reception.

42. The near-field microwave probe of claim 1, wherein said microwave electronics comprise microwave circuitry capable of producing pulses having a time duration within a range of 67 ps to 167 ps.

43. The near-field microwave probe of claim 1, wherein said second means for analyzing signals recorded by said first means comprises an algorithm.

44. The near-field microwave probe of claim 43, wherein said algorithm comprises a signal processing and recognition algorithm.

45. The near-field microwave probe of claim 44, wherein said signal processing and recognition algorithm is configured to determine whether or not there is a hematoma, and/or to estimate the thickness and/or the severity of a hematoma.

46. The near-field microwave probe of claim 1, wherein said second means for analyzing signals recorded by said first means comprise an algorithm that uses a set of characteristic hematoma signals from hematomas of different thicknesses and a predetermined threshold value which can be used for judging whether or not a hematoma signal from an actual patient represents a real blood pool or not.

47. The near-field microwave probe of claim 1, wherein said second means for analyzing signals recorded by said first means comprise:

- means for triggering a pulsed, swept range microwave device;
- means for performing several full range sweeps acquiring and returned signals;
- means for averaging said returned signals;
- means for subtracting a background signal and storing a resulting processed signal in memory;
- means for comparing the processed signal with stored characteristic hematoma signals; and
- means for estimating the hematoma thickness.

48. The near-field microwave probe of claim 1, wherein said antenna comprises a nozzle, the probe further comprising a calibration device attached to said housing, wherein said calibration device comprises an object for placement against said nozzle of said antenna.

49. The near-field microwave probe of claim 1, wherein said calibration device comprises several layers of material of varying dielectric constants.

50. The near-field microwave probe of claim 1, further comprising a hematoma detector cap for placement on a patient's head, wherein said cap is stretched over said patient's head, providing a clean smooth surface over which to do a scan of said near-field microwave probe.

51. The near-field microwave probe of claim 50, wherein said antenna comprises an aperture, wherein said cap has marked scan points numbered to direct a user in performing a scan of said patient's head, wherein said scan points are separated by a distance equal to the diameter of said aperture of said antenna to ensure complete coverage of said patient's head when scanned.

52. The near-field microwave probe of claim 51, wherein said cap comprises a microwave discernible identification pattern.

53. The near-field microwave probe of claim 50, wherein said cap comprises a firm, compliant and stretchable material.

54. The near-field microwave probe of claim 1, wherein said near-field microwave antenna comprises an enclosed GRIN lens with a planar reflector at its back end.

55. The near-field microwave probe of claim 1, wherein said near-field microwave antenna comprises an enclosed linear taper (cone) with a elliptical reflector at its back end.

56. The near-field microwave probe of claim 50, wherein said cap comprises a bar code.

57. The near-field microwave probe of claim 50, wherein said cap comprises a semiconductor identification chip.

* * * * *